(12) United States Patent
Frasher et al.

(10) Patent No.: US 7,966,199 B1
(45) Date of Patent: Jun. 21, 2011

(54) METHOD AND SYSTEM FOR IDENTIFICATION OF GEOGRAPHIC CONDITION ZONES USING AGGREGATED CLAIM DATA

(75) Inventors: Thomas A. Frasher, Sunnyvale, CA (US); Todd Matthew Fitch, Santa Clara, CA (US); Steven A. Sholtis, El Dorado Hills, CA (US)

(73) Assignee: Intuit Inc., Mountain View, CA (US)

( * ) Notice: Subject to any disclaimer, the term of this patent is extended or adjusted under 35 U.S.C. 154(b) by 943 days.

(21) Appl. No.: 11/780,427

(22) Filed: Jul. 19, 2007

(51) Int. Cl.
*G06Q 10/00* (2006.01)
(52) U.S. Cl. ............ 705/4; 705/2; 705/3; 701/200
(58) Field of Classification Search ............ 705/2–4; 701/200, 208; 345/642
See application file for complete search history.

(56) References Cited

U.S. PATENT DOCUMENTS

| 5,961,569 A * | 10/1999 | Craport et al. ............ 701/200 |
| 7,107,285 B2 * | 9/2006 | von Kaenel et al. ............ 1/1 |

* cited by examiner

*Primary Examiner* — Gerald J. O'Connor
*Assistant Examiner* — Linh-Giang Michelle Le
(74) *Attorney, Agent, or Firm* — Osha • Liang LLP

(57) ABSTRACT

A method for identifying a geographic condition zone, involving receiving a request for claim data, obtaining the claim data associated with a plurality of users, wherein the claim data comprises location data, filtering the claim data using a predefined condition to obtain filtered claim data, mapping the filtered claim data and the location data to appropriate locations in a geographic context to obtain mapped filtered claim data, and transmitting the geographic context comprising the mapped filtered claim data.

27 Claims, 7 Drawing Sheets

METHOD AND SYSTEM FOR IDENTIFICATION OF GEOGRAPHIC CONDITION ZONES USING AGGREGATED CLAIM DATA

BACKGROUND

Many programs are configured to collect information from various sources and aggregate the information before the information is reported. Based on the aggregated information, the programs may offer statistical analysis, trend reporting, aggregated graphing, and other useful information to the users of the aggregated information.

Often, aggregated information collected from various sources is presented in a geographic setting, allowing users to visualize the trends occurring for a particular event by geographic location. Geographic Information Systems (GIS) is one example of such a geographic backdrop against which aggregated information may be presented. GIS is a public standard set forth by the U.S. government that includes a collection of computer hardware, software, and geographic data for capturing, managing, analyzing, and displaying all forms of geographically referenced information.

The Center for Disease Control (CDC) is an example of an organization that uses GIS to present aggregated medical data. The CDC aggregates medical data from reported medical incidents and presents the aggregated medical data in a geographic setting in the form of an electronic map. Specifically, the CDC aggregates medical data obtained from reports provided by hospitals and physicians to determine disease outbreaks. In addition, the CDC also performs statistical analysis and trending on the aggregated medical data. For example, the CDC can use the aggregated medical data to determine the mortality rate associated with cancer by geographic area, race, and/or gender.

SUMMARY

In general, in one aspect, the invention relates to a method for identifying a geographic condition zone, comprising receiving a request for claim data, obtaining the claim data associated with a plurality of users, wherein the claim data comprises location data, filtering the claim data using a predefined condition to obtain filtered claim data, mapping the filtered claim data and the location data to appropriate locations in a geographic context to obtain mapped filtered claim data, and transmitting the geographic context comprising the mapped filtered claim data.

In general, in one aspect, the invention relates to a system for identifying a geographic condition zone, comprising a geographic repository comprising a geographic context, an aggregation engine configured to filter claim data using a predefined condition associated with the claim data to obtain filtered claim data, wherein the claim data is associated with a plurality of users and wherein the claim data comprises location data, and a mapping engine configured to map the filtered claim data and the location data to appropriate locations in the geographic context to obtain mapped filtered claim data, wherein the mapped filtered claim data is subsequently presented to a user.

In general, in one aspect, the invention relates to a method for identifying a geographic condition zone, comprising specifying a predefined condition based on which claim data associated with a plurality of users is filtered to obtain filtered claim data, wherein each claim in the claim data comprises location data and wherein the filtered claim data is mapped to appropriate locations in a geographic context to obtain mapped filtered claim data, and viewing the geographic context comprising the mapped filtered claim data.

In general, in one aspect, the invention relates to a method for identifying a geographic condition zone, comprising receiving a request comprising a predefined condition, generating a query comprising the predefined condition, sending the query to a claim source comprising claim data, wherein claim data comprises location data and wherein the claim data is filtered using the predefined condition to obtain filtered claim data, receiving the filtered claim data from the claim source, mapping the filtered claim data to a geographic context using the location data, and transmitting the geographic context comprising the mapped filtered claim data.

In general, in one aspect, the invention relates to a computer readable storage medium embodying instructions executable by the computer for identifying a geographic condition zone, the instructions comprising functionality to obtain a predefined condition, generate a request comprising the predefined condition, sending the request to obtain a geographic context comprising mapped filtered claim data, receive the geographic context comprising the mapped filtered claim data, wherein claim data is associated with a plurality of users, wherein each claim in the claim data comprises location data, wherein the claim data is filtered using the predefined condition to obtain filtered claim data, and wherein the filtered claim data is mapped to appropriate locations in the geographic context to obtain the mapped filtered claim data, and presenting the geographic context comprising the mapped filtered claim data.

Other aspects of the invention will be apparent from the following description and the appended claims.

DETAILED DESCRIPTION

Figure 1:
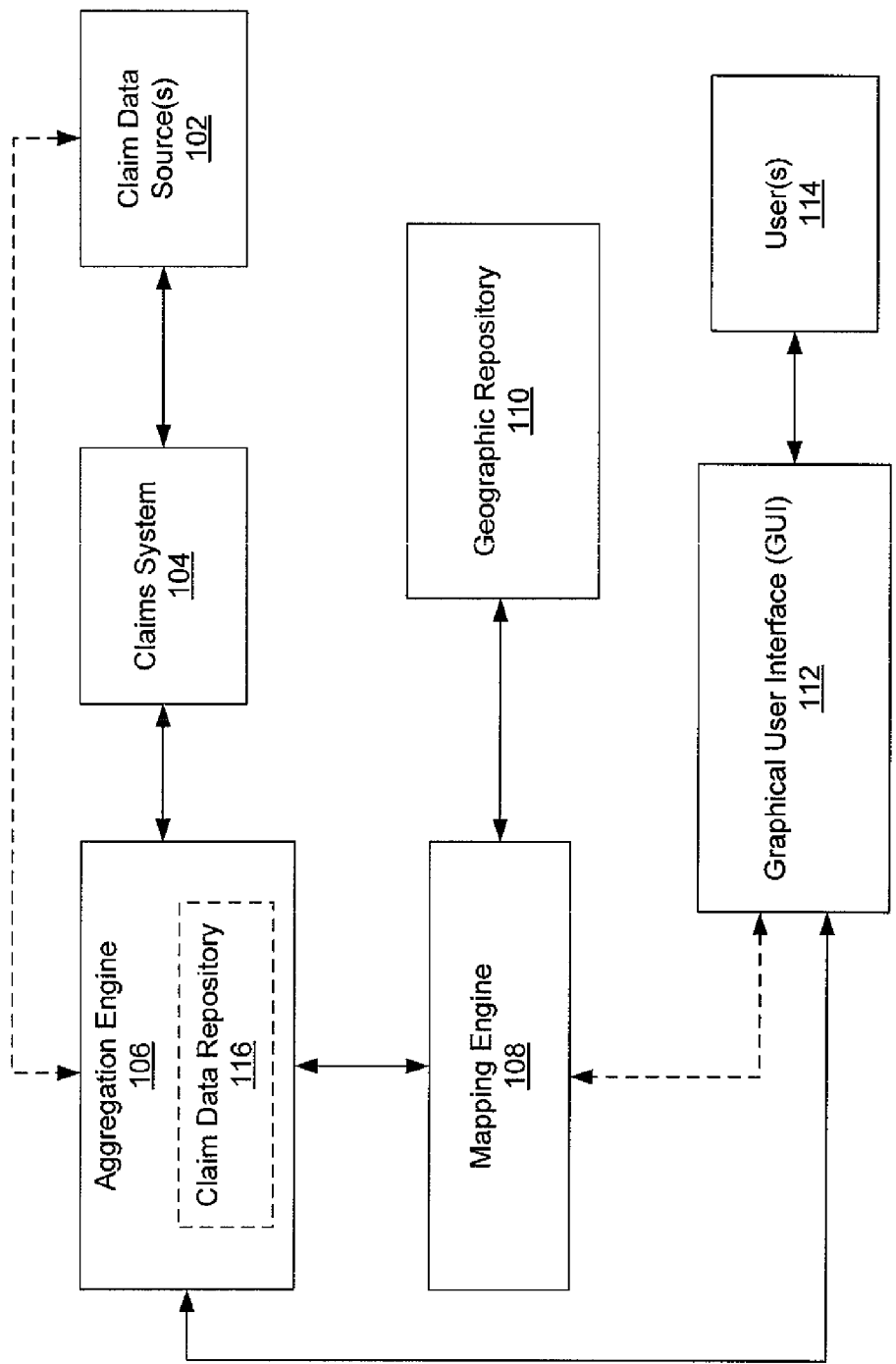
FIG. 1 shows a system in accordance with one or more embodiments of the invention.

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description. As used herein in the specification and figures, "ST" is essentially the same as "Step."

In general, embodiments of the invention provide a method and system for identifying geographic condition zones using claim data mapped in a geographic context. More specifically, embodiments of the invention provide a method and system for mapping filtered claim data obtained from a reimbursement provider in a geographic context, and identifying localized trends associated with a predefined condition in a geographic region.

FIG. 1 shows a system in accordance with one or more embodiments of the invention. Specifically, the system of FIG. 1 includes claim source(s) (102), a claim system (104), an aggregation engine (106), a mapping engine (108), a geographic repository (110), a graphical user interface (GUI) (112), and users (114). Each of the aforementioned components of FIG. 1 are described below.

In one or more embodiments of the invention, the claim data source(s) (102) corresponds to sources from which claim data is obtained. More specifically, the claim data source(s) may correspond to a server or other storage medium configured to store claim data associated with various reimbursement providers. Those skilled in the art will appreciate that the claim data source(s) may be proprietary storage devices, which are controlled, managed, and accessed by reimbursement providers. In one or more embodiments of the invention, reimbursement providers are entities that reimburse a user and/or a service provider for services rendered to the user (or at least paid for by the user). For example, a health insurance company (i.e., a reimbursement provider) may reimburse a user (i.e., the patient or a hospital or healthcare provider, which provided the healthcare services to the user). Alternatively, the health insurance company may directly reimburse the user for out-of-pocket expenses incurred.

In one or more embodiments of the invention, the reimbursement provider reimburses the entity that paid for the health services on behalf of the user who received the health services. In one or more embodiments of the invention, an insurance company may be considered a health insurance provider, a dental insurance provider, a vision insurance provider, an auto insurance provider, a housing insurance provider, or any other reimbursement provider.

Claim data stored in the claim data source(s) (102) includes data associated with a reimbursement claim filed with the reimbursement provider. For example, claim data may include medical claim data from medical claims (e.g., medical claims, dental claims, pharmacy claims, vision claims, etc.) submitted by or on behalf of members (i.e., users who are covered under a reimbursement provider plan offered by the reimbursement provider). Thus, claim data may be associated with multiple users that subscribe to a plan (e.g., a healthcare plan, an automobile insurance plan, housing insurance plan, etc.) that provides for reimbursement.

Further, in one or more embodiments of the invention, claim data stored in the claim data source(s) (102) includes condition(s) and location data. In one or more embodiments of the invention, conditions may be any parameter associated with claim data. For example, conditions associated with medical claim data may include symptoms and outbreaks of diseases or conditions, a cost of treatments and procedures, information on drugs prescribed by pharmacies or physicians, specific treatments assigned to a patient, and the effect of the assigned treatments (e.g., how quickly the patient recovered or deteriorated in response to an assigned treatment). Alternatively, if the claim source is an automobile insurance company, claim data may include conditions related to the vehicle type, the details of a vehicular incident reported to the automobile insurance company, the cost of the repair to the vehicle, vehicular theft information, the value of the vehicle involved in the claim, etc. Those skilled in the art will appreciate that claim data may be related to any type of reimbursement claim filed with a reimbursement provider and is not limited to the examples provided above. Further, those skilled in the art will appreciate that condition(s) may be any feature associated with claim data obtained from a particular claim data source.

In addition, in one or more embodiments of the invention, the location data included within claim data specifies the geographic location associated with the claim data. For example, if an automobile insurance claim is filed in the state of Florida, then the location data may specify that the claim data represents information filed by a user located in Florida. Those skilled in the art will appreciate that location data associated with claim data may be general or specific. For example, claim data may specify that the claim was filed in a particular country, or more specifically, may include a city name, a street address, latitude and longitude, or any other information used to specify the geographic location associated with the claim data.

In one or more embodiments of the invention, the claim data source(s) (102) is operatively connected to a claims system (104). The claims system (104) is a system used by reimbursement providers to process incoming claim data and store the claim data in the claim data source(s) (102). In one or more embodiments of the invention, the claims system (104) may be a front-end web server that communicates with the aggregation engine (106) on behalf of the reimbursement providers. Thus, the claims system (104) is configured to receive and process requests for claim data from the aggregation engine (106). In one or more embodiments of the invention, the claim data source(s) (102) and the claims system (104) may be hosted on a single server associated with one or more reimbursement providers. Further, those skilled in the art will appreciate that there may be different servers that host the claims system and the claim data source(s) for individual reimbursement providers.

Continuing with FIG. 1, in one or more embodiments of the invention, the aggregation engine (106) is configured to receive claim data from the claims system (104). More specifically, the aggregation engine (106) includes functionality to request and receive claim data from the claims system (104). Optionally, in one or more embodiments of the invention, the aggregation engine (106) may be configured to request claim data directly from the claim data source(s) associated with various reimbursement providers (i.e., if the reimbursement provider permits the aggregation engine (106) to directly access the claim data source(s) (102)). In one or more embodiments of the invention, the received claim data is optionally stored in a claim data repository (116) local to the aggregation engine (106). Those skilled in the art will appreciate that the claim data repository (116) may also be located external to the aggregation engine, in which case the aggregation engine may be operatively connected to the claim data repository (116).

Further, in one or more embodiments of the invention, the aggregation engine (106) is configured to receive a predefined condition (which may be provided by a user via the GUI (112)). The predefined condition may be any condition chosen to filter claim data, such as last name, city, zip code, sex, age, ethnicity, or other filterable term. In one or more embodiments of the invention, the aggregation engine (106) is configured to filter the claim data using the predefined condition to obtain filtered claim data. In one or more embodiments of the invention, the filtered claim data includes the predefined condition or, alternatively, information related to the predefined condition. In addition, in one or more embodiments of the invention, the filtered claim data specifically includes the number of incidences including the predefined condition in a particular geographic region. In one or more embodiments of the invention, the aggregation engine (106) is further configured to transmit the filtered claim data to the mapping engine (108) and receive mapped filtered claim data from the mapping engine (108).

In one or more embodiments of the invention, the mapping engine (108) is configured to receive the filtered claim data from the aggregation engine (106). In addition, the mapping engine (108) is configured to map the location data associated with each piece of filtered claim data to appropriate locations of a geographic context obtained from a geographic repository (110).

The geographic repository (110) is a storage device configured to store geographic contexts. Each geographic context describes the world (or a portion thereof) in geographic terms. More specifically, in one or more embodiments of the invention, the geographic contexts stored in the geographic repository (110) includes electronic maps. For example, electronic maps may include climate maps, topographical maps, road maps, political maps, physical maps, economic/resource maps, or any other type of map. In one or more embodiments of the invention, the geographic repository (110) may be a Geographic Information Systems (GIS) repository. Those skilled in the art will appreciate that the geographic repository (110) may include geographic contexts other than maps. For example, the geographic repository (110) may store data in the form of geographic analytical models, data structures that relate geographic data to other forms of data, and/or other types of geographic displays.

In one or more embodiments of the invention, the mapping engine (108) overlays the location data included within the filtered claim data with appropriate locations on a particular geographic context to obtain mapped filtered claim data. In one or more embodiments of the invention, the mapping engine (108) is configured to transmit the mapped filtered claim data to the aggregation engine (106). Alternatively, the mapping engine (108) may include functionality to directly transmit the mapped filtered claim data to the GUI (112). In one or more embodiments of the invention, the GUI (112) is part of a user application (not shown), executing on, for example, a web browser on a user computing device. Those skilled in the art will appreciate that the user computing device may be a personal computer, a laptop, a gaming device, a personal digital assistant, a mobile phone, or any other electronic device capable of displaying a GUI. Further, those skilled in the art will appreciate that other types of user interfaces may be used, such as textual interfaces that do not necessarily include a graphical display.

In one or more embodiments of the invention, the aggregation engine and the mapping engine may be hosted on a server (not shown) configured to provide a web service that facilitates the generation and transmission of geographic contexts including mapped claim data to users (or user systems).

In one or more embodiments of the invention, user(s) (114) may be any individual or entity configured to view, analyze, and identify geographic condition zones using the mapped filtered claim data. In one or more embodiments of the invention, a geographic condition zone is a geographic region that exhibits a localized trend associated with the predefined condition. For example, user(s) (114) may include researchers, reimbursement providers, healthcare providers such as physicians, hospitals, clinics, and/or users associated with the claim data (i.e., the users that subscribe to a particular reimbursement plan, such as patients that subscribe to a medical healthcare plan).

Those skilled in the art will appreciate that the aggregation engine (106) filters claim data obtained from claim data source(s) managed and controlled by reimbursement providers. Said another way, while the original reimbursement claims may be reported to the reimbursement provider by, e.g., healthcare personnel (such as physicians, hospitals, patients, individual users, or any other entity which reports reimbursement claims to reimbursement providers), the aggregation engine does not obtain claim data directly from healthcare personnel. Rather, the claim data used by the aggregation engine is obtained from claim data source(s) associated with reimbursement providers.

Figure 2A:
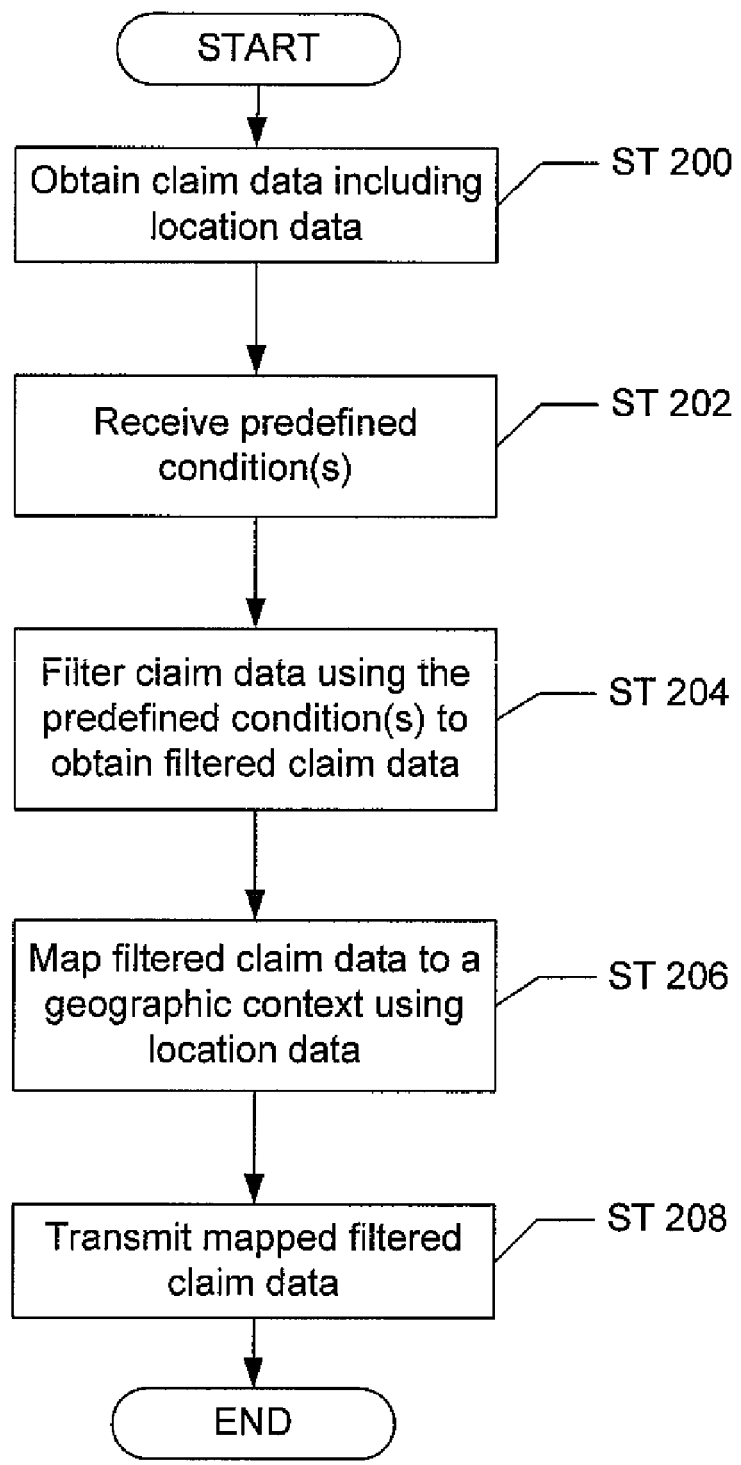
FIGS. 2A-2B and 3 show flow charts in accordance with one or more embodiments of the invention.

FIG. 2A shows a flow chart for obtaining mapped filtered claim data in accordance with one or more embodiments of the invention. In one or more embodiments of the invention, one or more of the steps shown in FIG. 2A may be omitted, repeated, and/or performed in a different order than that shown in FIG. 2A. Accordingly, the specific arrangement of steps shown in FIG. 2A should not be construed as limiting the scope of the invention. In ST 200, claim data (including location data) is obtained. In one or more embodiments of the invention, claim data may be obtained from one or more claim data source(s), either directly or indirectly via a claims system. In ST 202, predefined condition(s) are received. In one or more embodiments of the invention, the predefined condition(s) may be received from a user, via direct interaction with the GUI (112 in FIG. 1). In one or more embodiments of the invention, the predefined condition is a condition that is known before filtering of claim data is performed. As described above, predefined condition(s) may be one or more specific pieces of information associated with claim data by which claim data may be filtered. For example, if claim data is medical claim data, then predefined condition(s) may include, but are not limited to, an assigned treatment, a disease outbreak, a medical diagnosis, an effectiveness of an assigned treatment, a cost of a medical procedure, or any other information within the claim data that may be used to filter the claim data.

In ST 204, claim data is filtered using the predefined condition(s) to obtain filtered claim data (ST 204). In one or more embodiments of the invention, filtering claim data may involve extracting, from the claim data obtained in ST 200, the claim data that includes (or is associated with) the predefined condition(s) as parameters. Said another way, filtered claim data may be obtained by identifying each claim from the claim data obtained in ST 200 that includes (or is associated with) the predefined condition(s) as one of the information fields stored as part of the claim. Thus, in one or more embodiments of the invention, the filtered claim data may be a subset of the claim data originally obtained in ST 200. The filtered claim data may include a list of the claims including the predefined condition(s), a data structure including a table for each claim associated with the predefined condition(s), or any other representation of the claim data that is associated with the predefined condition(s).

Continuing with FIG. 2A, the filtered claim data is mapped to a geographic context using the location data included within each portion of filtered claim data (ST 206). More specifically, the location data associated with the filtered claim data is overlaid with appropriate locations on a geographic context, such as an electronic map. For example, if a portion of filtered claim data including the predefined condition(s) includes location data that specifies the claim was filed in Waxahachie, Tex., then the claim data may be mapped to an electronic map that represents the United States where the portion of filtered claim data may be mapped to the location Waxahachie, Tex. shown on the electronic map of the United States. The geographic context onto which filtered claim data is mapped may be obtained from a geographic repository that includes a variety of types of maps that represent the world (or portions thereof) in geographical terms. The geographic context including the mapped filtered claim data is transmitted (ST 208). In one or more embodiments of the invention, the geographic context including the mapped filtered claim data may be transmitted to the GUI (112 in FIG. 1), or any other application that requested the mapped filtered claim data.

Figure 2B:
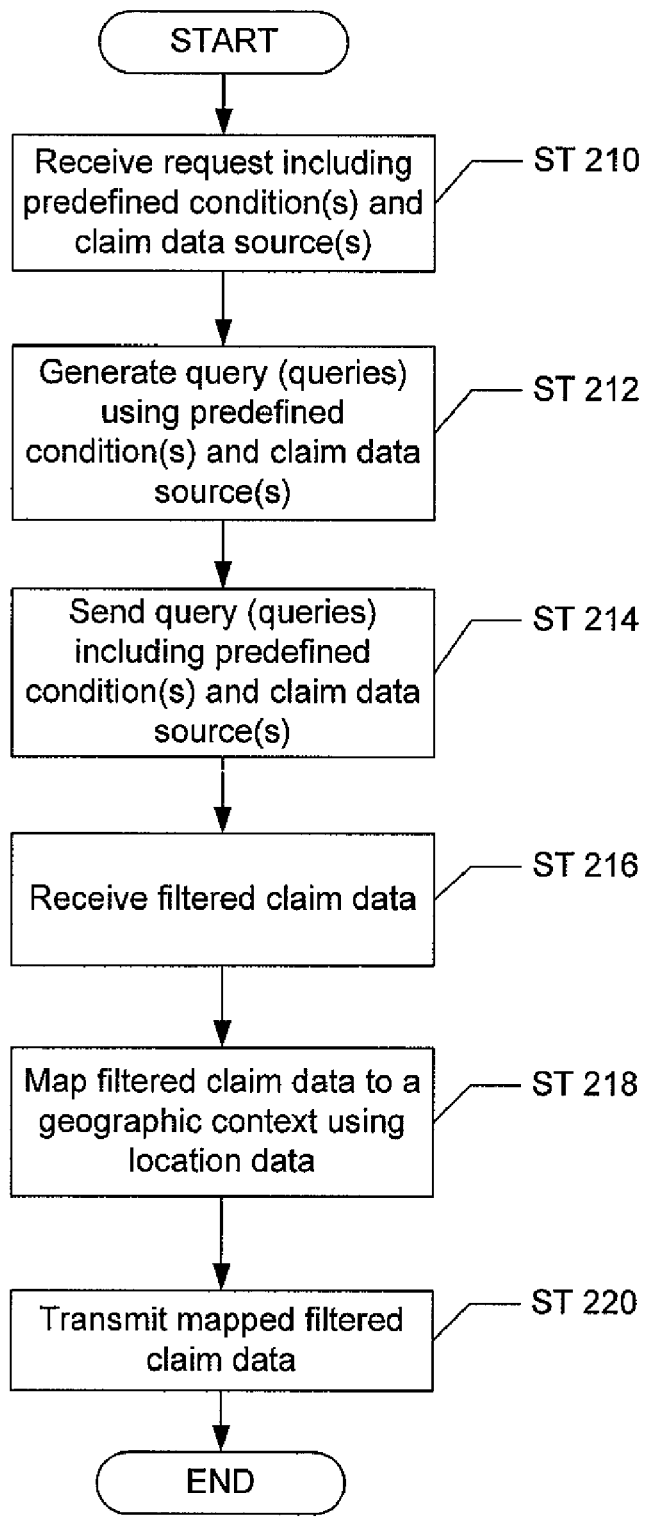

FIG. 2B shows a flow chart for presenting treatment options in accordance with one or more embodiments of the invention. In one or more embodiments of the invention, one or more of the steps shown in FIG. 2B may be omitted, repeated, and/or performed in a different order than that shown in FIG. 2B. Accordingly, the specific arrangement of steps shown in FIG. 2B should not be construed as limiting the scope of the invention.

FIG. 2B shows flow chart for obtaining mapped filtered claim data in accordance with one or more embodiments of the invention. In ST 210, a request including predefined condition(s) and claim data source(s) is received (ST 210). A query (queries) is generated using the received predefined condition(s) and claim data source(s) (ST 212). The generated query (queries) including the predefined condition(s) and claim data source(s) is sent directly to the claims data source(s) appropriate claims data source (directly or indirectly via a claims system) (ST 214). In one or more embodiments of the invention, the query (queries) for claim data may be generated by a web service that provides an interface between a user applications configured to request mapped filtered claim data and the reimbursement providers that control and manage the claim data. Further, the web service may be subscribed to by the user or user application requesting the mapped filtered claim data.

Continuing with FIG. 2B, because the query (queries) included the predefined condition(s), the claim data received in response to the transmitted query (queries) corresponds to filtered claim data (ST 216). Thus, the filtering of claim data may be performed by the claim data source(s) and/or the claims system to which the query (queries) was sent. The received filtered claim data is mapped onto a geographic context using the location data included within the filtered claim data (ST 218). The mapped filtered claim data is transmitted, for example, to a user application (ST 220).

Figure 3:
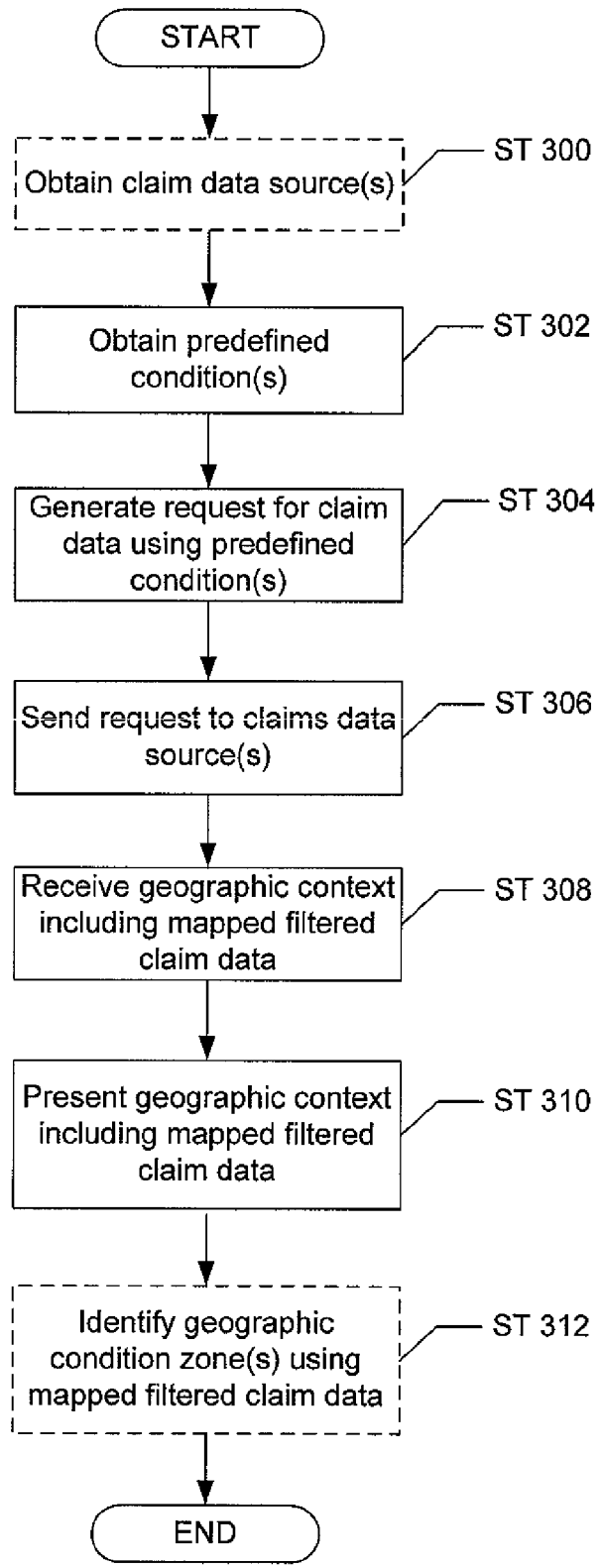

FIG. 3 shows a flow chart for presenting treatment options in accordance with one or more embodiments of the invention. In one or more embodiments of the invention, one or more of the steps shown in FIG. 3 may be omitted, repeated, and/or performed in a different order than that shown in FIG. 3. Accordingly, the specific arrangement of steps shown in FIG. 3 should not be construed as limiting the scope of the invention.

FIG. 3 shows a flow chart for identifying a geographic condition zone in accordance with one or more embodiments of the invention. More specifically, FIG. 3 shows a flow chart from the perspective of a user application that may request mapped filtered claim data. Claim data source(s) are optionally obtained (ST 300). For example, if a user provides particular claim data source(s) from which to obtain claim data, then claim data source(s) are obtained in ST 300. For example, a user may wish to identify geographic condition zones associated with medical diagnoses or medical treatments for a particular diagnosis. In this case, the user may specify that medical claim data from a healthcare reimbursement provider be obtained. Alternatively, a user may specify that claim data be obtained from pharmaceutical claim data sources, vision claim data sources, automobile claim data sources, housing claim data sources, any other claims data source, and/or any combination thereof.

The user application obtains predefined condition(s) from the user (ST 302). A request for claim data using the predefined condition(s) and optional claim data source(s) is generated (ST 304) and transmitted to claims data source(s) or a claims system (ST 306). The user application receives a geographic context including mapped filtered claim data (ST 308). The user application presents the received geographic context including the mapped filtered claim data to the user on a display device, such as on a monitor or other display device (ST 310).

In one or more embodiments of the invention, the user application may optionally include functionality to identify geographic condition zone(s) using the displayed mapped filtered claim data (ST 312). Alternatively, in one or more embodiments of the invention, a user using the user application may view the presented mapped filtered claim data and identify geographic condition zone(s). Geographic condition zone(s) are geographic regions that exhibit a localized trend associated with the predefined condition(s) on which the mapped filtered claim data is based. For example, if a predefined condition specified by a user requested claim data including a medical diagnosis of cancer, the geographic context including the mapped filtered claim data may present a geographic representation of all the medical claims that include cancer as a medical diagnosis for a patient. Using the mapped filtered claim data, a user or user application may identify a geographic region that exhibits a growth in cancer diagnoses, a dearth in cancer diagnoses, or other trend associated with cancer diagnoses.

Those skilled in the art will appreciate that embodiments of the present invention may be used to identify local geographic trends for non-medical data as well. Said another way, the invention is not limited to the medical arena, and may be used determine a localized geographic trend for a particular predefined condition for any type of aggregated and/or filtered data. For example, the present invention may be used to identify geographic weather trends, user spending trends for marketing and/or advertising purposes, or trends in auto insurance claims associated with auto accidents or vehicular crimes. As a more specific example, the present invention may be used to identify particular geographic regions that prepare for hurricane season by purchasing large amounts of generators, plywood, and water. Alternatively, for example, the present invention may be used to observe which geographic areas around the world experience a higher than average rate of auto accidents.

Further, in one or more embodiments of the invention, the format of the geographic context that includes the mapped filtered claim data may be user-defined. More specifically, user application or user, via the user application, may define how the claim data is displayed on the geographic context. For example, the claim data may be displayed when a user clicks on a particular geographic location or symbol on the geographic context. Alternatively, placing a mouse or other input device over a particular geographic location on the geographic context may result in a pop-up window that displays additional information related to the claim data associated with the chosen geographic location. In one or more embodiments of the invention, the user may request that the geographic context show only the geographic locations associated with the mapped filtered claim data using a symbol or icon, without any text associated with each mapped filtered claim data portion. In addition, a user may define the shape, size, shading, color, and/or other visual characteristics of the symbols/icons shown on a geographic context. Those skilled in the art will appreciate that there may be multiple methods for displaying text and/or geographic locations associated with the filtered claim data, and the invention is not limited to the aforementioned examples.

Figure 4A:
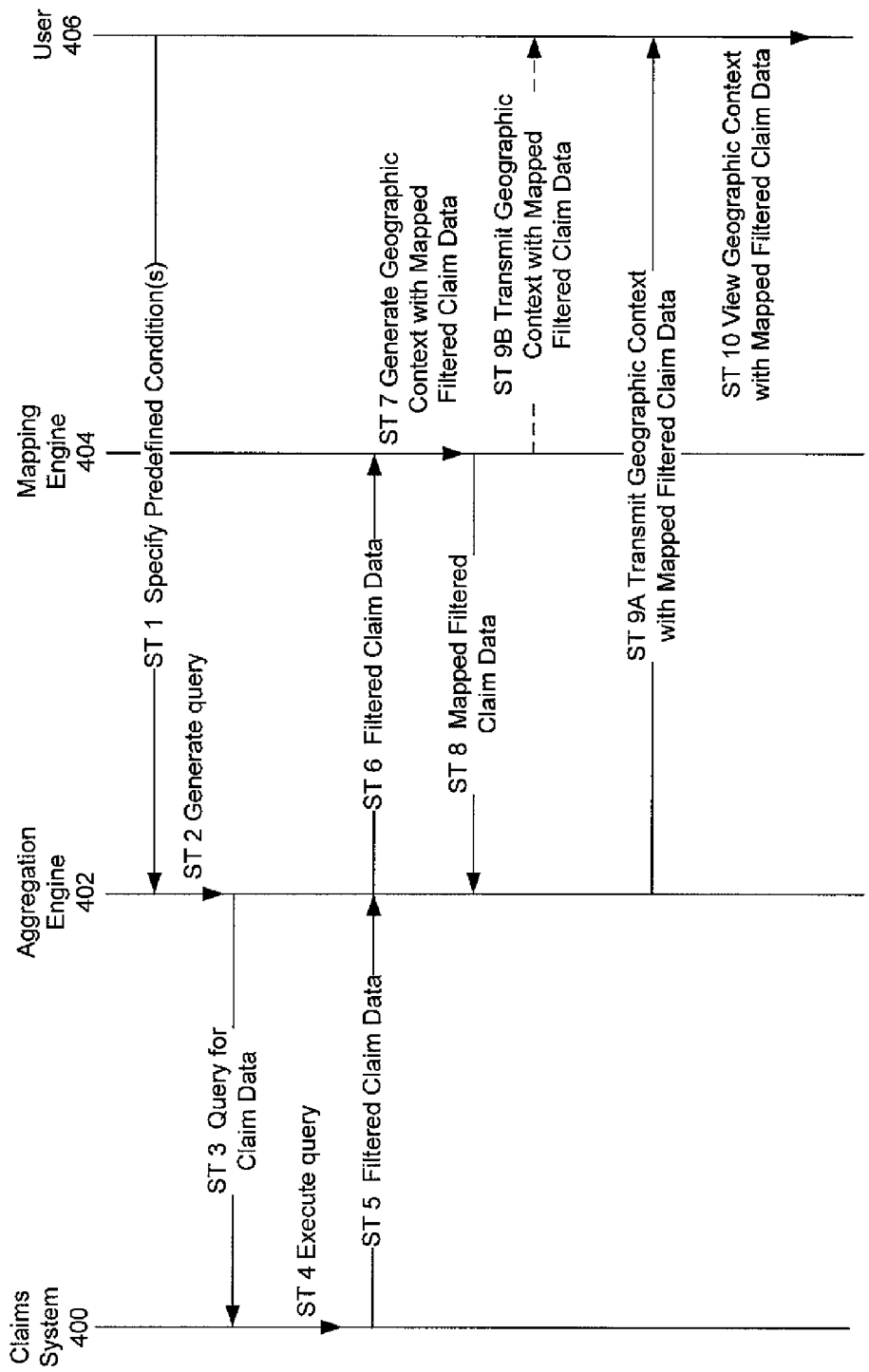
FIGS. 4A-4B show examples in accordance with one embodiment of the invention.

FIG. 4A shows an example of the interaction between various components of the present invention in accordance with one or more embodiments of the invention. More specifically, in one or more embodiments of the invention, FIG. 4A shows an example of the interaction between the claims system (400), the aggregation engine (402), the mapping engine (404), and an end-user (406). The following example is not intended to limit the scope of the invention. In one or more embodiments of the invention, one or more of the steps shown in FIG. 4A may be omitted, repeated, and/or performed in a different order than that shown in FIG. 4A. Accordingly, the specific arrangement of steps shown in FIG. 4A should not be construed as limiting the scope of the invention.

Initially, a user (406), via a user-application, specifies a predefined condition(s). The predefined condition(s) is then sent to the aggregation engine (402) (ST 1). In one or more embodiments of the invention, the user (406) may also specify a type of claim data (e.g., medical claim data, automobile claim data, housing claim data, and/or pharmaceutical claim data). Alternatively, the type of claim data to request may be determined by the aggregation engine (402) using the predefined condition(s) obtained from the user (406). As described above, the predefined condition(s) may be any condition(s) associated with which a geographic trend may be viewed. For example, the user (406) may specify to geographically view the claim data associated with drivers that have had their hub caps stolen. In this case, the predefined condition specified by the user may be "vehicular theft" or "hub cap theft." Alternatively, the user (406) may wish to geographically view claim data for user spending habits.

Subsequently, the aggregation engine (402) generates a query for claim data associated with the predefined condition(s) (ST 2). The generated query is then sent to the claims system (400) (ST 3). The claims system (400) executes the query (ST 4) to obtain the claims data, filters the claims data, and transmits the filtered claim data to the aggregation engine (402) (ST 5). In one or more embodiments of the invention, the claim data may be transmitted from the claim system (400) (or directly from the claim data source(s)) to the aggregation engine (402)) using a claim data transfer (CDT) protocol. In one or more embodiments of the invention, the CDT protocol is similar to the HCDT protocol, discussed in detail in application Ser. No. 11/799,170, entitled "Method and System For Healthcare Data Exchange," herein incorporated by reference. In this scenario, the filtering and aggregation of claim data is performed by the claims system and the claim data source(s) associated with a particular reimbursement provider corresponding to the type of claim data requested by the aggregation engine.

At this stage, the aggregation engine (402) sends the filtered claim data to the mapping engine (404) (ST 6). The mapping engine (404) maps the filtered claim data onto a geographic context obtained from a geographic repository (ST 7) and transmits the geographic context including the mapped filtered claim data to the aggregation engine (402) (ST 8). The aggregation engine (402) sends the geographic context with the mapped filtered claim data to the user (406) (or more specifically, to a user system including a computing device configured to present the geographic context and the mapped filtered claim data to the user) (ST 9A).

Alternatively, in one or more embodiments of the invention, the mapping engine (404) may be configured to send the geographic context including the mapped filtered claim data to the user (or user system) (ST 9B). Finally, the user (406), via the user system, may view the geographic context including the mapped filtered claim data to identify one or more geographic condition zones associated with the specified predefined condition(s) (ST 10). For example, using the automobile claim data example from above, if the predefined condition(s) specified by the user was "vehicular theft claims," then the user may identify geographic regions in which vehicular theft (and specifically hub cap theft) has risen in the last year. Alternatively, the user may identify the make and/or model of the vehicles that experience hub cap theft in different geographic regions.

In one or more embodiments of the invention, the geographic context including the mapped filtered claim data may be used to identify zones of disease outbreak. For example, claim data obtained by the aggregation engine may originate from a health insurance provider. Further, predefined condition(s) specified by a user may request claim data that is associated with a medical diagnosis made by a healthcare provider (e.g., a physician). By plotting such claim data onto a geographic context, geographic regions that exhibit a disease outbreak may be identified.

Figure 4B:
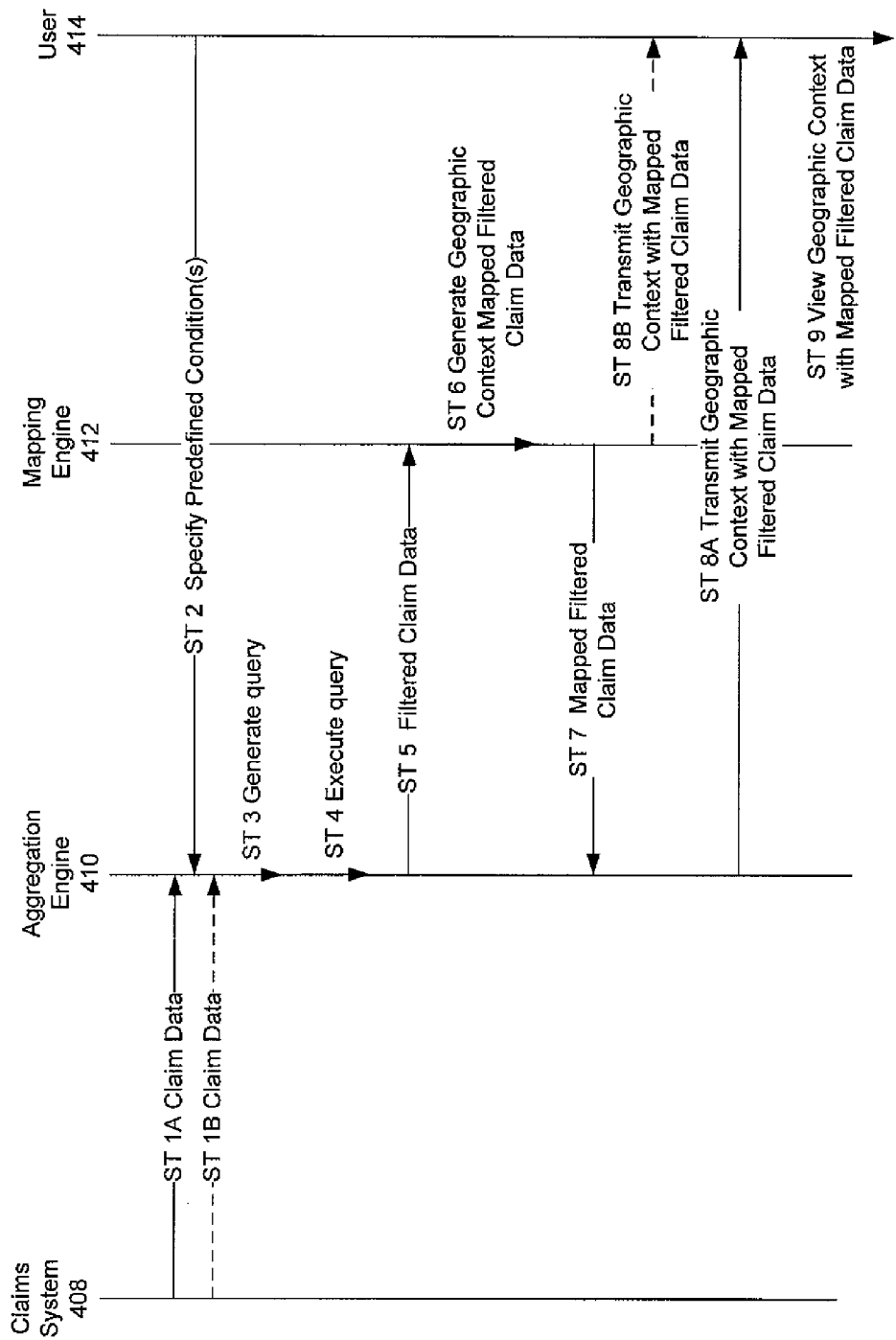

FIG. 4B shows example in accordance with one or more embodiments of the invention. In one or more embodiments of the invention, one or more of the steps shown in FIG. 4B may be omitted, repeated, and/or performed in a different order than that shown in FIG. 4B. Accordingly, the specific arrangement of steps shown in FIG. 4B should not be construed as limiting the scope of the invention. Initially, claim data is transmitted from the claims system (408) to the aggregation engine (410) (ST 1A). More specifically, in one or more embodiments of the invention claim data is transmitted by the claims system (400) to the aggregation engine (402) when an update or new piece of claim data is stored in the claim data source(s) associated with the claims system (400). Alternatively, the aggregation engine (402) may poll for updated or new claim data from the claims system (400) periodically (ST 1B). Thus, claim data may be received by the aggregation engine (402) before or after predefined condition(s) are received from a user (406).

A predefined condition(s) is received by a user (406) (ST 2). Using the predefined condition(s) and the claim data, the aggregation engine (410) generates and executes a query (ST 3, ST 4). In one or more embodiments of the invention, the query generated and executed by the aggregation engine (410) filters the received claim data using the predefined condition(s) to obtain filtered claim data. Subsequently, the filtered claim data is sent to the mapping engine (412) (ST 5). The mapping engine (412) is responsible for mapping the filtered claim data to a geographic context to generate a geographic context that includes the mapped filtered claim data plotted to appropriate geographic locations (ST 6). The mapping engine (412) then sends the mapped filtered data to the aggregation engine (410) (ST 7). At this stage, the aggregation engine sends the generated geographic context including the mapped filtered claim data to the user (414) (ST 8A).

Alternatively, in one or more embodiments of the invention, the mapping engine (412) may directly send the generated geographic context including the mapped filtered claim data to the user (414) or user system (not shown) (ST 8B). Finally, the geographic context is viewed by the user (414) to identify one or more geographic condition zones associated with the predefined condition(s) (ST 9).

Figure 5:
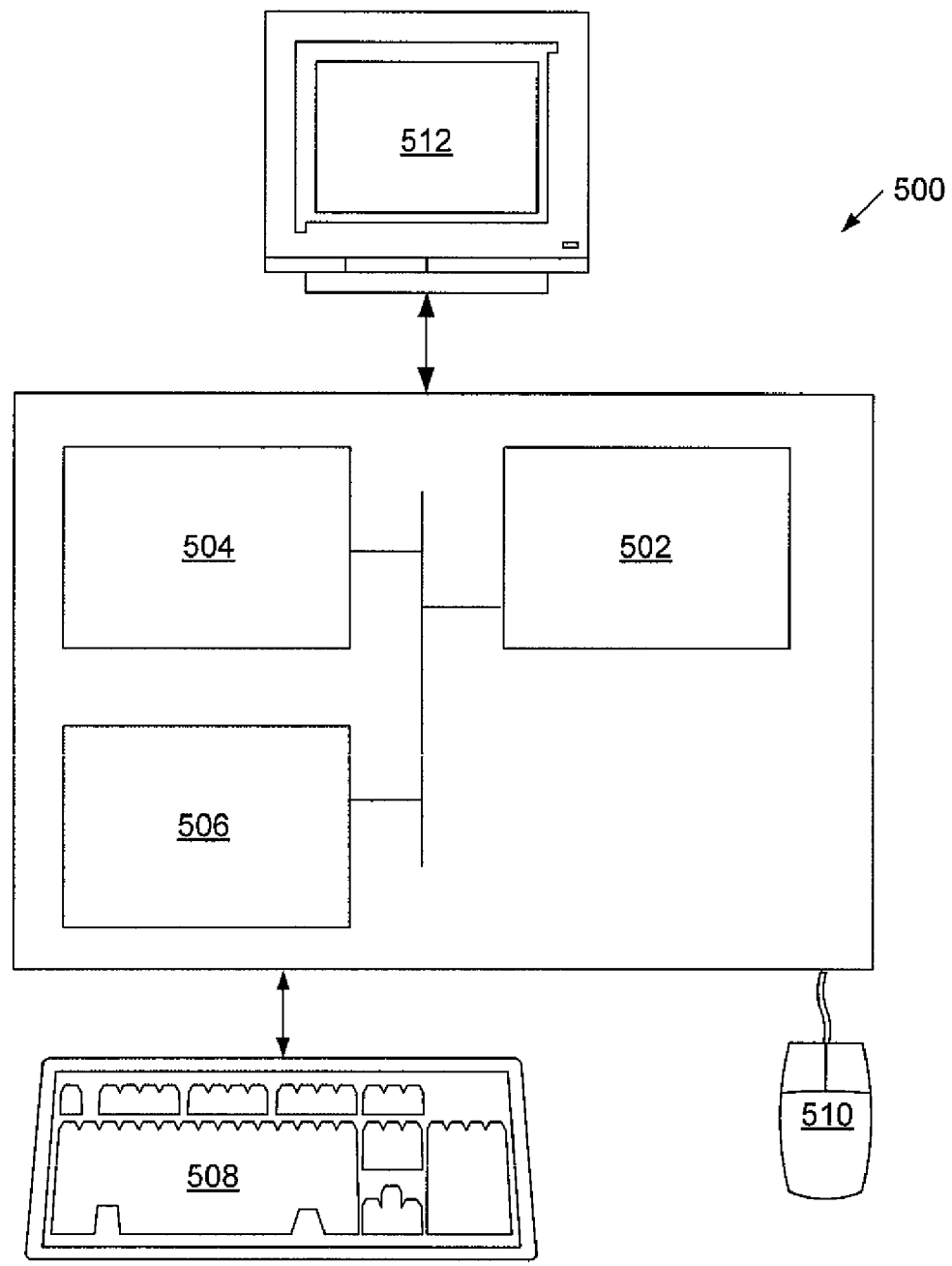
FIG. 5 shows a computer system in accordance with one or more embodiments of the invention.

The invention may be implemented on virtually any type of computer regardless of the platform being used. For example, as shown in FIG. 5, a computer system (500) includes a processor (502), associated memory (504), a storage device (506), and numerous other elements and functionalities typical of today's computers (not shown). The computer (500) may also include input means, such as a keyboard (508) and a mouse (510), and output means, such as a monitor (512). The computer system (500) is connected to a local area network (LAN) or a wide area network (e.g., the Internet) (not shown) via a network interface connection (not shown). Those skilled in the art will appreciate that these input and output means may take other forms.

Further, those skilled in the art will appreciate that one or more elements of the aforementioned computer system (500) may be located at a remote location and connected to the other elements over a network. Further, the invention may be implemented on a distributed system having a plurality of nodes, where each portion of the invention (e.g., the mapping engine, the aggregation engine, the claims system, the geographic repository, etc.) may be located on a different node within the distributed system. In one embodiment of the invention, the node corresponds to a computer system. Alternatively, the node may correspond to a processor with associated physical memory. The node may alternatively correspond to a processor with shared memory and/or resources. Further, software instructions to perform embodiments of the invention may be stored on a computer readable medium such as a compact disc (CD), a diskette, a tape, a file, or any other computer readable storage device.

Embodiments of the invention provide a system and method for identifying geographic condition zones using mapped filtered claim data. Specifically, embodiments of the invention obtain information from reimbursement providers, which are entities that typically aggregate and store a wide scope of information for each user or service provider associated with a reimbursement claim, including the cost of procedures performed, the geographic location of the incident described by the filed claim, etc. This information is subsequently plotted onto a geographic context such that geographic condition zones can be identified and analyzed by researchers, reimbursement provider personnel, users associated with the claim data, or any other party that may be interested in identifying geographic condition zones. More specifically, embodiments of the invention provide a method for early detection of geographic condition zones, which may be used to determine more effective solutions for geographic regions that exhibit a negative trend (such as a high rate of vehicular crimes or an outbreak of a particular medical disease). Alternatively, the early detection of geographic condition zones may also be used to implement procedures (such as marketing and advertising or medical treatments) to take advantage of a positive trend in consumer spending or effectiveness of a particular medical treatment.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for identifying a geographic condition zone, comprising:
    receiving a request for claim data,
        wherein the request comprises a predefined condition and a claim data source, and
        wherein the predefined condition is a parameter associated with claim data from the claim data source;
    generating, using a processor, a query based on the predefined condition and the claim data source;
    sending, using the processor, the query to the claim data source, wherein the claim data source executes the query to obtain filtered claim data;
    receiving, using the processor, a transmission comprising the filtered claim data from the claim data source,
        wherein the transmission is sent by the claim data source using a claim data transfer protocol,
        wherein the filtered claim data is associated with a plurality of users, and
        wherein the filtered claim data comprises location data;
    mapping, using the processor, the filtered claim data and the location data to appropriate locations in a geographic context to obtain mapped filtered claim data;
    transmitting, using the processor, the geographic context comprising the mapped filtered claim data; and
    identifying, using the processor, a geographic condition zone using the mapped filtered claim data, wherein the geographic condition zone corresponds to a geographic region that comprises a localized trend associated with the predefined condition.

2. The method of claim 1, wherein the predefined condition is one selected from a group consisting of a disease outbreak, a medical condition, an assigned medical treatment, a weather condition, an effectiveness of an assigned medical treatment, a crime condition, a consumer spending condition, and a vehicular accident condition.

3. The method of claim 1, further comprising:
    receiving the predefined condition from a user.

4. The method of claim 1, wherein the geographic context comprises an electronic map, and wherein the electronic map is displayed in one selected from a group consisting of two-dimensions, three-dimensions, and four-dimensions.

5. The method of claim 4, wherein a format of the geographic context is user-defined.

6. The method of claim 1, wherein claim data comprises at least one selected from a group consisting of medical claims, dental claims, pharmaceutical claims, vision claims, housing insurance claims, and automobile insurance claims.

7. The method of claim 6, wherein the medical claims comprise at least one selected from a group consisting of data associated with a cost for a medical procedure, data associated with an assigned treatment, data associated with an effectiveness of an assigned treatment, data associated with prescribed drugs for an assigned treatment, data associated with symptoms of a medical condition, data associated with treatment options for a medical condition, and data associated with a diagnosed medical condition.

8. The method of claim 1, wherein the geographic context is obtained from a geographic repository, and wherein the geographic repository is a Geographic Information Systems repository.

9. The method of claim 1, wherein filtering the claim data comprises:
    aggregating, using the processor, the filtered claim data to determine a number of claims associated with the predefined condition in a geographic region within the geographic context.

10. The method of claim 1, wherein the plurality of users are associated with a reimbursement provider, and wherein claim data is data associated with a request for reimbursement from the reimbursement provider.

11. The method of claim 10, wherein the plurality of users are patients, and wherein the reimbursement provider is a healthcare provider.

12. A system for identifying a geographic condition zone, comprising:
    a processor;
    a persistent storage device;
    a display device;
    a geographic repository comprising a geographic context, wherein the geographic repository is stored using a persistent storage device;

an aggregation engine executing on the processor and configured to:
  receive a request for claim data,
    wherein the request comprises a predefined condition and a claim data source, and
    wherein the predefined condition is a parameter associated with claim data from the claim data source;
  generate a query based on the predefined condition and the claim data source;
  send the query to the claim data source, wherein the claim data source executes the query to obtain filtered claim data;
  receive a transmission comprising the filtered claim data from the claim data source, wherein the transmission is sent by the claim data source using a claim data transfer protocol,
    wherein the claim data is associated with a plurality of users and wherein the claim data comprises location data; and
a mapping engine executing on the processor and configured to map the filtered claim data and the location data to appropriate locations in the geographic context to obtain mapped filtered claim data,
  wherein the mapped filtered claim data is subsequently presented to a user using the display device,
  wherein the mapped filtered claim data is used to identify a geographic condition zone, and
  wherein the geographic condition zone corresponds to a geographic region that comprises a localized trend associated with the predefined condition.

13. The system of claim 12, wherein the geographic context is obtained from a geographical repository and wherein the geographical repository is a Geographic Information Systems repository.

14. The system of claim 12, wherein the predefined condition is one selected from a group consisting of a disease outbreak, a medical condition, an assigned medical treatment, a weather condition, an effectiveness of an assigned medical treatment, a crime condition, a consumer spending condition, and a vehicular accident condition.

15. The system of claim 12, wherein the geographic context comprises an electronic map, and wherein the electronic map is displayed in one selected from a group consisting of two-dimensions, three-dimensions, and four-dimensions.

16. The system of claim 15, wherein a format of the geographic context is user-defined.

17. The system of claim 12, wherein claim data comprises at least one selected from a group consisting of medical claims, dental claims, pharmaceutical claims, vision claims, housing insurance claims, and automobile insurance claims.

18. A method for identifying a geographic condition zone, comprising:
  specifying, using a processor, a predefined condition,
    wherein the predefined condition is a parameter associated with claim data from a claim data source,
    wherein the predefined condition is used to generate a query, using the processor, for execution by the claim data source,
    wherein filtered claim data is obtained using a claim data transfer protocol from the claim data source upon execution of the query by the claim data source,
    wherein each claim in the claim data comprises location data, and
    wherein the filtered claim data is mapped, using the processor, to appropriate locations in a geographic context to obtain mapped filtered claim data;
  viewing the geographic context comprising the mapped filtered claim data, when the geographic context is transmitted to a display device; and
  identifying, using the processor, a geographic condition zone using the mapped filtered claim data, wherein the geographic condition zone corresponds to a geographic region that comprises a localized trend associated with the condition.

19. The method of claim 18, further comprising:
  specifying, using the processor, the claim data source, wherein the claim data source is a persistent storage device.

20. The method of claim 18, wherein the claim data source is one selected from a group consisting of a medical claims source, a dental claims source, a pharmaceutical claims source, a vision claims source, a housing insurance claims source, and an automobile insurance claims source.

21. The method of claim 18, wherein the predefined condition is one selected from a group consisting of a disease outbreak, a medical condition, an assigned medical treatment, a weather condition, an effectiveness of an assigned medical treatment, a crime condition, a consumer spending condition, and a vehicular accident condition.

22. The method of claim 18, wherein the filtered claim data is mapped, using the processor, to appropriate locations in the geographic context using the location data associated with the filtered claim data.

23. The method of claim 22, wherein the geographic context is obtained from a geographic repository, and wherein the geographic repository is a Geographic Information Systems repository.

24. The method of claim 18, wherein the plurality of users are associated with a reimbursement provider, and wherein claim data is data associated with a request for reimbursement from the reimbursement provider.

25. The method of claim 24, wherein the plurality of users are patients, and wherein the reimbursement provider is a healthcare plan to which the plurality of users subscribe.

26. The method of claim 18, wherein the claim data is obtained from a claim data source, and wherein the claim data source is a persistent storage device.

27. A computer readable storage medium embodying instructions executable by the computer for identifying a geographic condition zone, the instructions comprising functionality to:
  receive a request for claim data,
    wherein the request comprises a predefined condition and a claim data source, and
    wherein the predefined condition is a parameter associated with claim data from the claim data source;
  generate a query based on the predefined condition and the claim data source;
  send the query to the claim data source, wherein the claim data source executes the query to obtain filtered claim data;
  receive a transmission comprising the filtered claim data from the claim data source,
    wherein the transmission is sent by the claim data source using a claim data transfer protocol,
    wherein the filtered claim data is associated with a plurality of users, and
    wherein the filtered claim data comprises location data;
  map the filtered claim data and the location data to appropriate locations in a geographic context to obtain mapped filtered claim data;

transmit the geographic context comprising the mapped filtered claim data; and identify at least one geographic condition zone using the mapped filtered claim data, wherein the at least one geographic condition zone corresponds to a geographic region that comprises a localized trend associated with the predefined condition.

\* \* \* \* \*